United States Patent [19]
Bernard et al.

[11] Patent Number: 5,580,777
[45] Date of Patent: Dec. 3, 1996

[54] GENERATION OF NEURAL PRECURSOR CELL LINES

[75] Inventors: Ora Bernard, North Balwyn; Perry F. Bartlett, North Carlton, both of Australia

[73] Assignee: Amrad Corporation Limited, Australia

[21] Appl. No.: 330,114

[22] Filed: Oct. 27, 1994

Related U.S. Application Data

[63] Continuation of Ser. No. 935,357, Aug. 27, 1992, abandoned, which is a continuation of Ser. No. 536,423, filed as PCT/AU88/00423, Oct. 28, 1988, abandoned.

[30] Foreign Application Priority Data

Oct. 29, 1987 [AU] Australia ................... 5131/87

[51] Int. Cl.⁶ .............. C12N 15/00; C12N 5/00
[52] U.S. Cl. ............. 435/240.2; 435/172.3; 435/320.1
[58] Field of Search .............. 435/172.3, 320.1, 435/240.2

[56] References Cited

U.S. PATENT DOCUMENTS 5,270,191  12/1993  McKay ................... 435/172.3

OTHER PUBLICATIONS

Cory et al Oncogene Research 1:61. 1987.
Bartlett et al PNAS 85:3255. 1988.
Casalbon et al Nature 326:188, 1987.
Ekhterae, et al., Blood, 75:365–9 (1990).
Bernard, et al., J. Neurosi. Res. 24:9–20 (1989).
Bartlett, et al., Proc. Nat. Acad. Sci., 85:3255–59 (1988).
Ryder, et al., J. Neurobiol., 21:356–75 (1990).
Murphy, et al., J. Neurobiology, 22:522–35 (1991).
Enrietto, et al., Cell, 35:369–79 (1983).
Langdon et al., "Growth of Eµ–myc Transgenic B–Lymphoid Cells in Vitro and Their Evolution Towards Autonomy", *Oncogene Research*, vol. 3: pp. 271–279, 1988.
Hayflick (1964) "The Limited In Vitro Lifetime of Human Diploid Cell Strains", *Experimental Cell Research* 37, 614–636.
Walker et al., eds., (1988) *The Language of Biotechnology, A Dictionary of Terms*, American Chemical Society, Washington, D.C.

*Primary Examiner*—Suzanne E. Ziska
*Attorney, Agent, or Firm*—Scully, Scott, Murphy & Presser

[57] ABSTRACT

A method for the in vitro production of lines of immortalized neural precursor cells, including cell lines having neuronal and/or glial cell characteristics, comprises the step of infecting neuroepithelium or neural crest cells with a retroviral vector carrying a member of the myc family of oncogenes.

12 Claims, 8 Drawing Sheets

GENERATION OF NEURAL PRECURSOR CELL LINES

This is a continuation of application(s) Ser. No. 07/935,357 filed on Aug. 27, 1992, now abandoned, which is a file wrapper continuation of Ser. No. 07/536,623 filed Jun. 28, 1990, now abandoned corresponding to PCT/AU88/00423 filed Oct. 28, 1988.

This invention relates to the generation of neuroepithelial and neural crest cell lines that are capable of differentiating in vitro into cells expressing neuronal and/or glial cell markers. In particular, the invention relates to the immortalisation of neural precursor cells contained in neuroepithelium and neural crest cells by the introduction of members of the myc family of oncogenes in a retrovirus vector.

Whilst the detailed description herein relates specifically to the generation of mouse neuroepithelial and neural crest cell lines, it will be understood that the invention is not restricted to murine cell lines and that in fact it extends to cell lines of other mammalian species including humans.

The two major cell types in the mammalian central nervous system, neurons and glia, are developmentally derived from the neuroepithelium that forms the neural tube. Neuroepithelial cells have been shown to give rise to both types of neural cells in vitro (1,2) and precursor cells committed to a particular cell lineage have been identified within mouse neuroepithelial cells as early as embryonic day 10 (E10)(3). The factors and genes that regulate precursor cell differentiation in the mammalian nervous system are largely unknown, and the establishment of cell lines representative of these neural precursor populations would greatly assist in their identification.

Work leading to the present invention has included the generation of cell lines derived from mouse E10 neuroepithelial cells by the introduction of the c-myc oncogene with a murine retrovirus delivery system using the pDol vector (17). These cell lines have the characteristics and surface phenotype of freshly isolated E10 neuroepithelial cells. They express cytokeratin but do not express neuronal or glial cell markers,.and can be induced to express class I histocompatibility antigens upon stimulation with interferon-$_\gamma$ ($_\gamma$ IFN). While they do not differentiate spontaneously in vitro, exposure to basic fibroblast growth factor (bFGF) induces their differentiation into neurofilaments positive neurons and glial fibrillary acidic protein (GFAP) positive glial cells.

It has also been found that different types of mouse neuroepithelial and neural crest cell lines can be generated by the introduction of a different recombinant retroviral vector bearing the N-myc, the c-myc or the L-myc oncogenes and that some of these cell lines have the capacity to differentiate spontaneously in vitro into neurons and/or glial cells. Many of these lines are factor dependent and can be used as target populations to rapidly screen for the potential neurotrophic factors. These cell lines can also be used for the production of factors important for the maintenance of replication and differentiation of cells in the central and peripheral nervous systems. Finally, these immortalised cell lines may also be used as model systems to study the possibility of using cell lines to restore damaged brain after an accident, stroke or in diseases such as Parkinson, Huntington, Alzeheimer, etc.

The myc proto-oncogene family has at least four different members: c-myc, N-myc, L-myc (see reference 4 for review), and the recently cloned B myc (5). The first three share the ability of being able to compliment a mutated ras gene in the transformation of primary rat embryo fibroblasts (6–9). They are expressed in the developing brain, in E10 neuroepithelium and during embryogenesis, but no expression can be detected two weeks after birth (10). Furthermore, N-myc is also expressed in neuroblastomas and is frequently amplified in these tumours (4). L-myc is expressed in small cell carcinoma of the lung, however brain tumours expressing L-myc have not been identified.

The effects of retroviruses bearing the different myc gene on differentiation of E10 neuroepithelial cells has been investigated by the generation of immortalised mouse neuroepithelium cell lines using new retroviral vectors pZen and pZenSVNeo (11) bearing the c-myc, the N-myc or the L-myc proto-oncogenes. These zen retroviruses express higher levels of the inserted genes than the vector (pDol) used previously. The majority of the new cell lines spontaneously differentiate into mature neural cells without the addition of exogenous growth factors.

According to the present invention, there is provided a method for the in vitro production of immortalised neural precursor cells, which comprises the step of infecting neuroepithelium or neural crest cells with a retroviral vector carrying one of the myc oncogenes.

Preferably the myc oncogene carried by the retroviral vector is the c-myc, the N-myc or the L-myc oncogene.

The present invention also extends to immortalised or continuous cell lines which are neuroepithelial or neural crest cells Which have been infected with a retroviral vector carrying one of the myc oncogenes.

In addition to immortalisation of the neural precursor cells, in certain instances the infection of these cells with a retroviral vector carrying one of the myc oncogenes has been found to produce cell lines having neuronal and/or glial cell characteristics.

In particular embodiments of this invention, the pDol vector (17) has been used to construct a Dol(c-myc) retrovirus which gives rise to continuous lines resembling freshly isolated neuroepithelium cells, and the pZen and pZenSV-Neo vectors (11) have been used to give Zen(myc) viruses (including c-myc, N-myc and L-myc) that give rise to cells capable of differentiating in vitro.

Members of the myc family of oncogenes are not capable of directly transforming primary cells such as mouse embryo fibroblasts but are capable of immortalising these cells. Normally, growth of mouse embryo fibroblasts in vitro is limited to about 60 generations, however, after introduction of the c-myc oncogene the cells become immortalised and grow forever (12). These immortalised cells have growth characteristics of normal cells and they do not develop into tumors when injected into nude mice (13). This capacity of the myc oncogenes to immortalise cells has been used in the present invention to generate cell lines of embryonic neural cells.

All the cells of the central nervous system (CNS) are derived from the neuroepithelium which forms the neural tube (14). The cells of the peripheral nervous system are derived from the neural crest cells which migrate from the neural tube (15). The neuroepithelial cells can give rise, in culture, to glial cells and to neurons but these cells survive in culture only for a very limited period of time (1,2). Studies on early brain development have been difficult to perform but the use of cell lines represents a major leap forward in the technology to study these processes. In addition, isolation of homogeneous populations of cells from normal mouse brain are also very difficult to obtain in large numbers. Therefore the myc oncogenes have been used in order to generate continuous cell lines representing brain cells during different stages of brain differentiation. The cell lines so obtained:

1. are immortalised;
2. have the capacity to differentiate in vitro into neurons or glial cells; and
3. have the capacity to respond to growth factors such as basic fibroblast growth factor (bFGF) (16) and also growth factors produced by themselves and other neuroepithelium cell lines.

Further details of the present invention are set out in the following specific Examples. It will be appreciated that while the specific examples relate to work done in the mouse cells, the techniques and procedures are equally applicable to human cells.

Figure 1A:
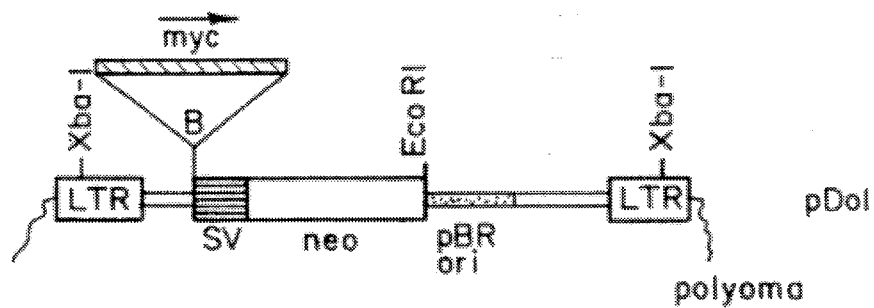
FIG. 1 shows
(A) schematic representation of recombinant retroviral plasmid used to produce the Dol(c-myc) retrovirus. The expression of the c-myc gene is controlled by the promoter and enhancer in the Moloney long terminal repeats (LTRs). The Neo$^R$ gene is expressed through the simian virus 40 early promoter and enhancer (SV). pBRori is the pBR322 origin of replication. R, EcoRi; B, BamHI: X, XbaI.
(B) Southern blot analysis of DNA from neuroepithelium (lanes NE) and neuroepithelial cell lines (lanes 2.3Q, 2.3D.12, and 2.3D)(25). Cellular DNA (2 μg) was digested with EcoRI (RI) or XbaI (X), size-fractionated on 0.7% agarose, and transferred onto a Zeta-Probe membrane (Bio-Rad) in 0.4M NaOH. The filter was hybridised to $^{32}$P-labelled c-myc cDNA clone (19). Hybridisation and washing conditions were as described (19a). Solid arrowheads mark the position of the endogenous c-myc-bearing fragments, and the open arrowheads indicate the proviral c-myc DNA bands. Sizes of fragments are in kilobase pairs. The intensities of the bands in various lanes vary because of unequal amounts of cDNA loaded onto the gel.

FIG. shows expression of MPZenSVNeo(N-myc) recombinant retroviruses in neuroepithelial cell lines. Poly(A)$^+$ RNA was prepared from E10 neuroepithelial cells (lane 1), MPZenSVNeo(N-myc) infected NE cell lines (lanes 2–6), neuroblastoma C1300N2a (lane 7). The filter was first hybridised to N-myc probe then stripped off and hybridised to c-myc and actin probes. Sizes of transcripts are in kilobases (kb). 2.3 and 2.9 transcripts represent cellular c-myc and N-myc respectively. The proviral transcripts are 6 and 5.6 kb. The 5.6 kb transcripts are not resolved in the over exposed lanes (lanes 2,5,6) and are not detectable in the under exposed lane (lane 3).

Figure 6:
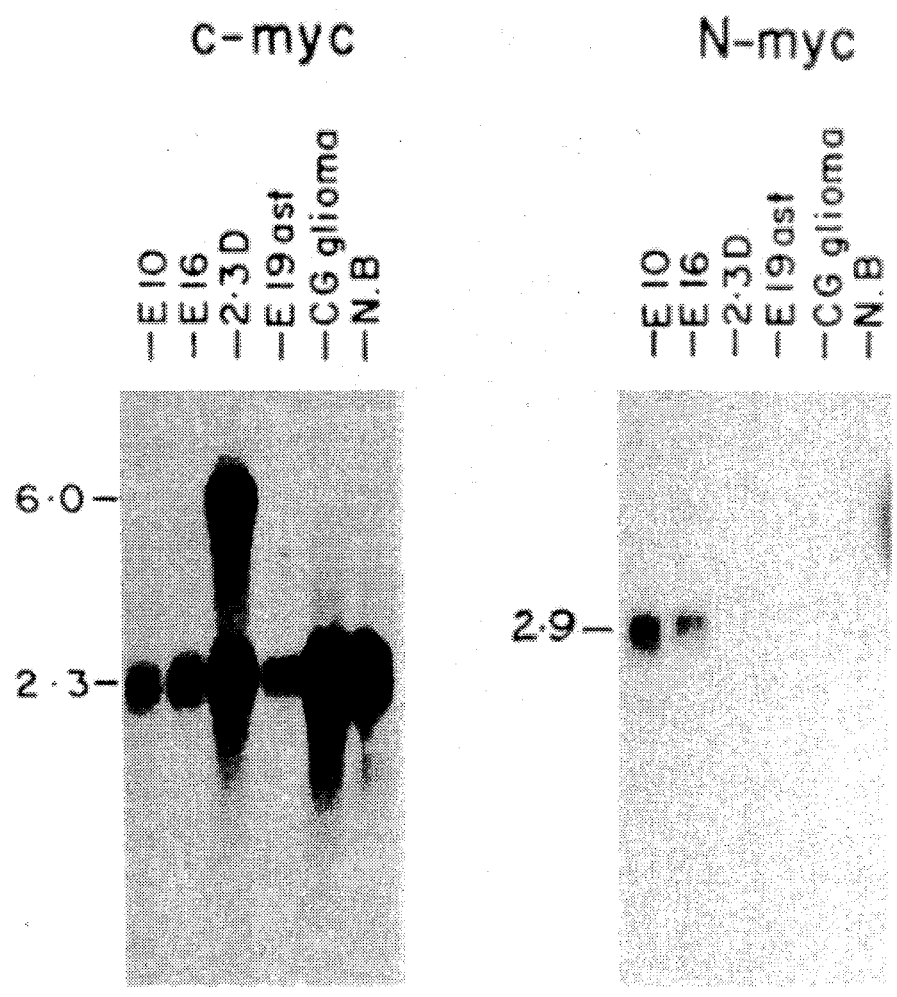

FIG. 6 shows expression of c-myc and N-myc in embryonic brain. Poly(A)$^+$ RNA was prepared from E10 neuroepithelium (E10) brain of 16-day old embryo (E16) and neuroepithelial cell lines infected with Dol(c-myc) virus (2.3D). Astroglia were from cultured populations of 19-day embryo cerebellar cells (E19 ast), glioma cell line (CG glioma) and neuroblastoma c1300N2a (NB). The filter was hybridised to c-myc probes, stripped off and hybridised to a N-myc probe.

Figure 7:
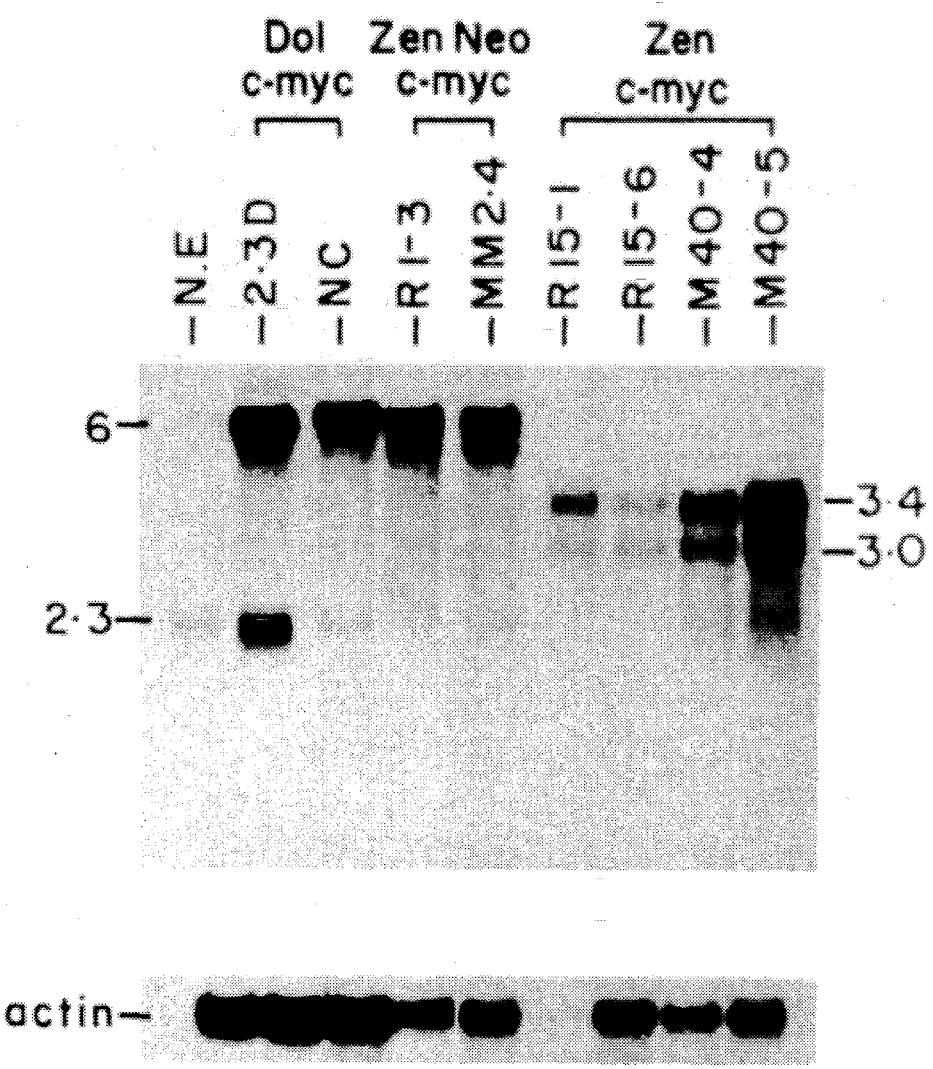

FIG. 7 shows expression of c-myc in Zen(c-myc) based virus infected neuroepithelial cell lines. Poly(A)$^+$ RNA was prepared from E10 neuroepithelial cells (NE), Dol(c-myc) infected neuroepithelial cell line (2.3D), ZenSVNeo(c-myc) (R1.3) and MPZenSVNeo(c-myc) (MM2.4) virus infected neuroepithelial cell lines, and Zen(c-myc) (R15.1, R15.6) and MPZen(c-myc) (M40.4, M40.5) infected neuroepithelial cell lines. Cellular c-myc is 2.3 kb, the proviral transcripts in the ZenSVNeo(c-myc) lines are 5.1 and 4.7 kb while those from the Zen(c-myc) lines are 3.4 and 3.0 kb.

Figure 8:
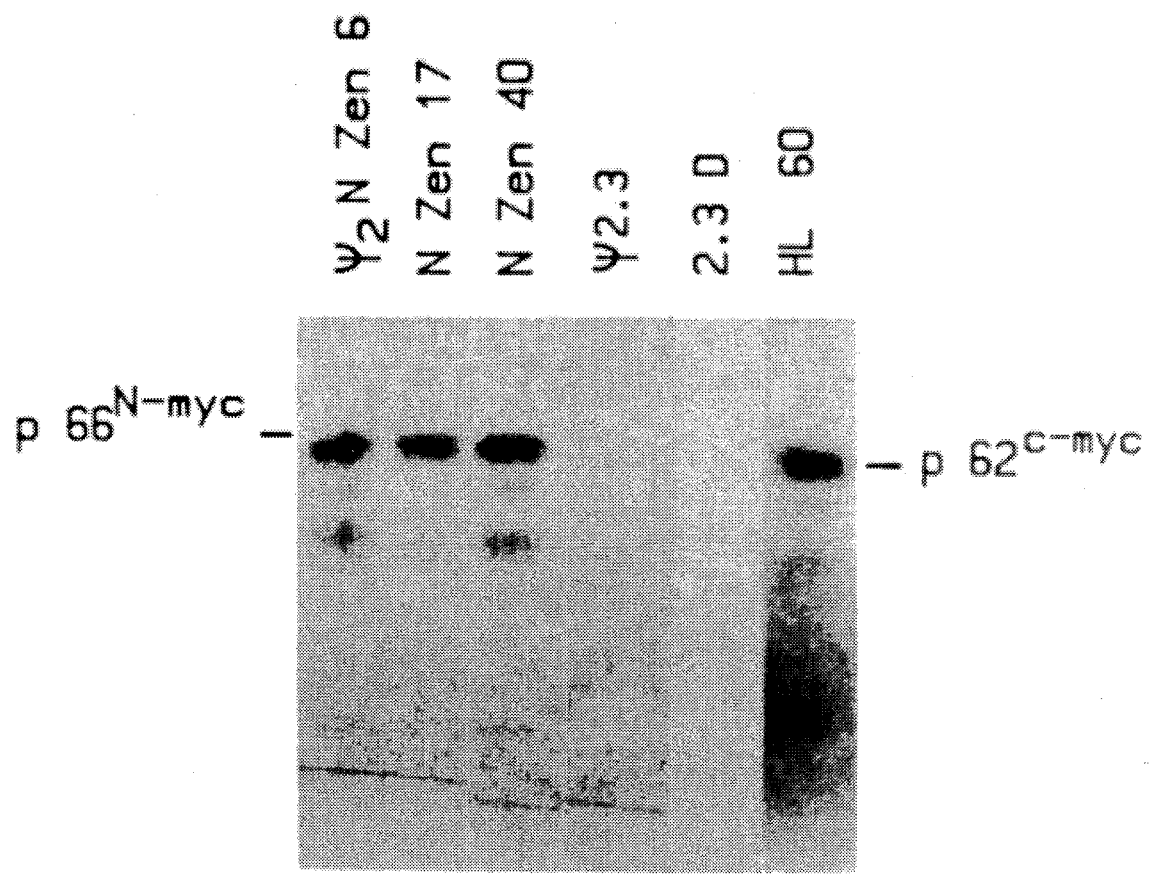

FIG. 8 shows Western blot analysis of myc protein expressed in the different cell lines. $\psi_2$ NZen6-$\psi_2$ line producing MPZenSVNeo(N-myc) virus; NZen17 and NZen 40—neuroepithelial cell lines generated by infected with the MPZenSVNeo(N-myc) virus. $\psi$2.3–$\psi_2$ line producing Dol(c-myc) virus; 2.3D—neuroepithelial cell line generated by infection of neuroepithelial cells with Dol(c-myc) virus; HL-60—promyelocytic cell line.

EXAMPLE 1

(a) Materials and Methods

Construction of Dol(c-myc) Retrovirus

The c-myc retrovirus used to infect neuroepithelial cells was constructed by using the shuttle vector pDol as described (17). This vector carries the bacterial neomyocin resistance (Neo$^R$) gene that confers resistance to the antibiotic G418 (18). The Xho I fragment of the murine c-myc cDNA was inserted into the BamHI site of the pDol vector. This fragment contains the entire c-myc coding region (19). A schematic diagram of the recombinant retroviral plasmid is shown in FIG. 1A. To avoid possible effects induced by a helper virus in subsequent experiments, virus stocks were produced by transfection of $\psi$-2 fibroblasts (20) with the retroviral vector. Transfected $\psi$-2 cells were selected for resistance to G418, and a cell line producing the highest titer of the c-myc virus ($10^4$ viruses per ml) was used for all the experiments.

Infection of Neuroepithelial Cell

Virus-producing ψ-2 cells were cultured in 24-well Linbro plates in 1 ml of Dulbecco's modified Eagle's medium (DMEM) supplemented with 10% (vol/vol) fetal calf serum at $5\times10^3$ cells per well and were irradiated with 2800 rads. After 24 hr, single-cell suspensions of neuroepithelial cells isolated from mesencephalon of 10 day embryo CBA/CaH mice were cultured on the irradiated cells at various concentrations ranging from $10^3$ to $5\times10^5$ cells per well. After culturing the cells for 2–5 days, 400 μg of Genetecin (G418) (GIBCO) was added to each well, and fresh medium containing G418 was subsequently added every 3–4 days. Cell lines were cloned by limiting dilution by using 3T3 fibroblasts as an underlayer.

Immunofluorescent Staining

Cell lines were cultured on glass coverslips contained in 24-well Linbro plates at a density of $2\times10^3$ cells per ml. After incubation for 48 hr coverslips were removed and transferred to a humidified Terasaki plate. To stain for surface antigenic determinants, 50 μl of the primary antibody was added per coverslip and incubated for 30 min at room temperature. Coverslips were washed by gentle immersion into beakers of isotonic phosphate-buffered saline (PBS), and 50μl of fluorescein-labelled second antibody was applied to each coverslip and incubated for a further 30 min. Coverslips were washed as before and fixed by the addition of acid alcohol [95% (vol/vol) absolute ethanol and 5% (vol/vol) acetic acid] for 20 min at –20°C. The coverslips were inverted and mounted in glycerol containing 2.6% (wt/vol) 1,4-diazobicyclo-[2.2.2]octane (Dabco, Merck, Melbourne, Australia). To visualise the glial fibrillary acidic protein (GFAP) antigen and the neurofilament proteins, cells were fixed in acid alcohol prior to the addition of the primary antibody.

Biological Reagents

A2B5, an anti-ganglioside antibody (21), was used at a dilution of 1:100 of ascites fluid. Anti-GFAP antibody was a polyclonal antiserum from Dakopatts (Sydney, Australia) and was used at a dilution of 1:30. Anti-neurofilament antibody (22) was obtained from Immuno Nuclear (Stilwater, Minn) and was used at a dilution of 1:150. K2F2, an anti-cytokeratin antibody (23), was obtained from D.Hewish (CSIRO, Melbourne, Australia) and was used at a dilution of 1:100. WEHY-NEP-6, an anti-glial cell precursor monoclonal antibody, was prepared in our laboratory (3) and used at a dilution of 1:10. Anti-H-$2K^k$ monoclonal antibody was from hybridoma clone 11-4.1 and anti-$IA^k$ monoclonal antibody was from hybridoma clone 10-2.16 (24); both hybridomas were obtained from the American Type Culture Collection.

Acidic FGF from bovine brain was obtained from R & D Systems (Minneapolis, Minn). Recombinant bovine basic FGF was obtained from Collaborative Research (Waltham, Mass). Recombinant interferono γ was obtained from Genentech (South San Francisco, Calif.).

(b) RESULTS

Infection of Neuroepithelial Cells

To maximise the efficiency of infection, neuroepithelial cells were co-cultivated with the virus-producing ψ-2 cell lines. A ψ-2 line producing equivalent titers of the pDol virus carrying the $Neo^R$ gene was used as a control. The majority (>98%) of the neuroepithelial cells used for the infection expressed the cytokeratin intermediate filament marker as shown by immunofluorescent staining with the antibody K2F2, indicating that this population was not significantly contaminated with mesenchymal elements. The G418-resistant cells were evident 7–10 days after the addition of the drug, whereas, in control cultures containing only neuroepithelium, all the cells were dead within 48 hr of G418 addition. After 10–14 days of culture, no ψ-2 cells survived, leaving only the infected neuroepithelial cells to proliferate. Dol(Neo) virus-infected cells grew slowly and only survived for 2–3 months. In marked contrast, cells infected with Dol(c-myc) virus grew rapidly after an initial lag period of 1–2 weeks and have continued to proliferate for>12 months. The frequency of precursors capable of giving rise to $Neo^R$ cell lines was assessed by limiting dilution and found to be 2×10.

Clonality of the Cell Lines

Figure 1B:
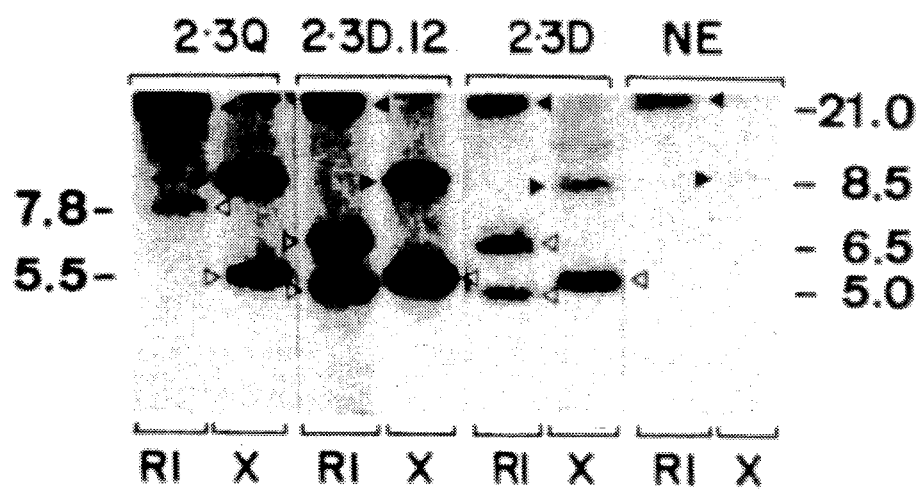

To establish that the cell lines did indeed harbour c-myc virus and to investigate their clonal composition, DNA from selected lines was digested with EcoRI with XbaI restriction endonucleases and subjected to Southern blot analysis (25) with a radioactive c-myc probe. Fib.1B shows the results for the lines 2.3Q and 2.3D as well as for 2.3D.12, which is a clonal derivative of 2.3D. Xba I cuts within each proviral long terminal repeat, releasing a 5.5-kilobase fragment. Since, for 2.3Q cells, the intensity of this band was about half that of the 8.5-kilobase fragment from the endogenous c-myc alleles, it is clear that this line carries only a single provirus and is, therefore, clonal. The line 2.3D harbours multiple inserts, as judged by the relative intensity of the Xba I fragments. Individual proviral inserts can be distinguished in EcoRI digests: there is only one EcoRI site within the provirus, and the size of the released fragment thus depends on the location of the nearest EcoRI site in the flanking DNA. By this criterion, 2.3D cells carry three inserts, two within EcoRI fragments of similar size. Since the number and size of the proviral fragments was identical in the subclone 2.3D.12 (FIG. 1B), the 2.3D line is also clonal.

EXPRESSION oF c-myc mRNA

Figure 2:
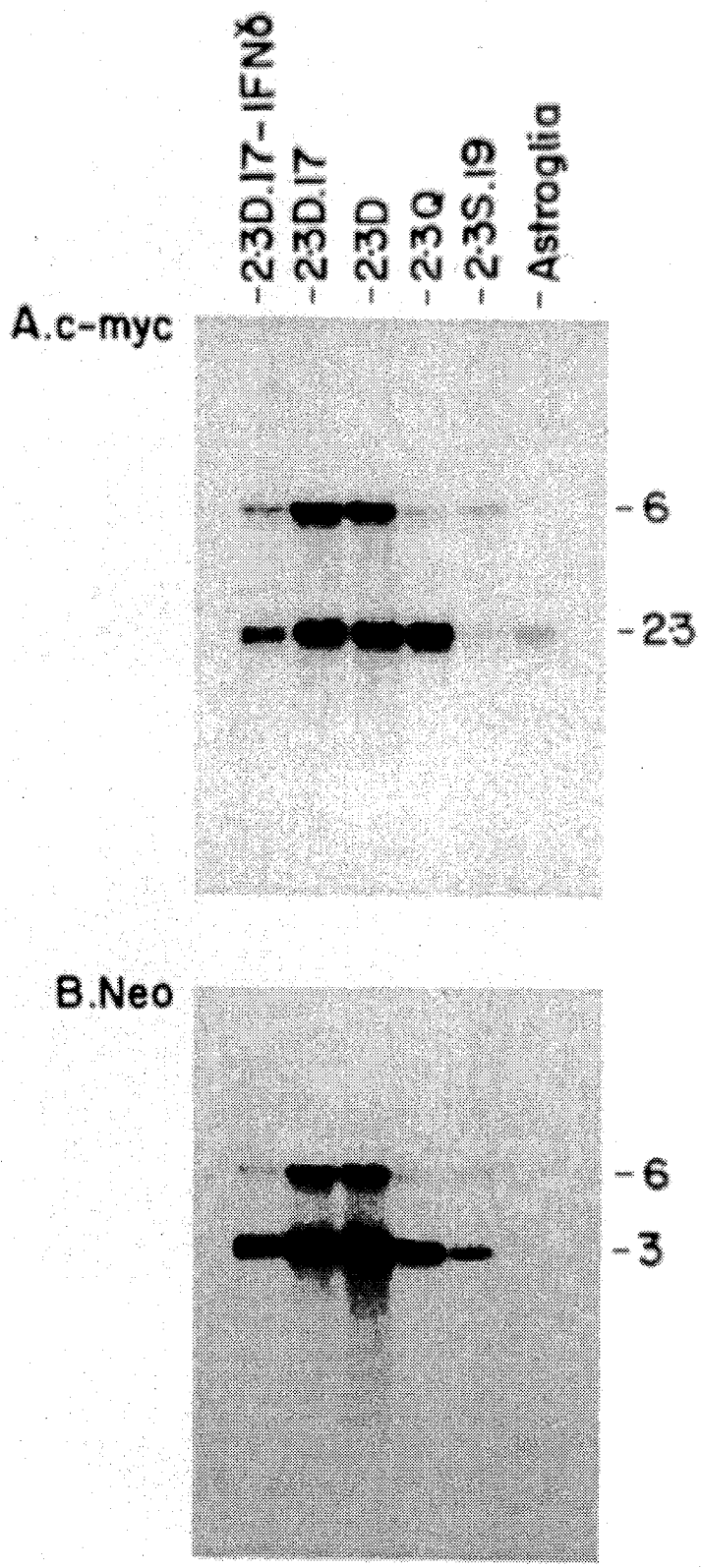
FIG. 2 shows
(A) Expression of c-myc in neuroepithelial cell lines. Poly(A)$^+$ RNA from several cell lines (indicated above the lanes) was fractionated on a formaldehyde/agarose gel and transferred to nitrocellulose filters for hybridisation with $^{32}$P-labelled probe (19a). The c-myc probe was as above and the Neo probe was a 1.4-kilobase HindIII-Sal I fragment from pSV2Neo (18). Lines 2.3D.17 and 2.3S.19 are clones isolated from 2.3D and 2.3S cell lines, respectively. Astroglia were from cultured populations of 19 day embryo cerebellar cells.
(B) The same filter was hybridised to a $^{32}$P-labelled Neo probe. The full size viral RNA corresponds to the 6-kilobase transcript hybridising to the c-myc probe; the smaller 3-kilobase RNA corresponds to the subgenomic simian virus 40-Neo mRNA. The amount of poly(A)$^+$ RNA loaded onto the gel for the 2.3S.19 cells and the astroglia was at least 3 times lower than in other lanes.

Analysis of mRNA from several neuroepithelial cell lines for c-myc expression showed that both the proviral and endogenous c-myc genes are expressed in all cell lines (FIG. 2A). As expected from the number of integrated proviruses, the level of the 6-kilobase proviral c-myc transcript is higher in the 2.3D line than in the 2.3Q line. Significantly, the 2.3-kilobase endogenous c-myc transcript is expressed in all the lines examined. Thus, the introduction of the proviral c-myc gene has not silenced the endogenous c-myc gene. This result contrasts with those obtained for B lymphocytes in transgenic mice carrying a c-myc oncogene driven by the immunoglobulin heavy chain enhanced, where no expression of the endogenous c-myc gene could be detected (26,27). However, it is similar to that reported for some fibroblast cell lines where expression of the endogenous c-myc gene is not suppressed by the introduced c-myc gene (28).

Tumorigenicity of the Neuroepithelial Cell Lines

The c-myc virus-infected cells were not tumorigenic. Syngeneic animals injected with $5\times10^6$ cells from several lines were monitored for 3 months, but no tumours were detected. Thus, by itself, deregulated c-myc expression appears not to be sufficient to transform neuroepithelial cells. However, after continual passage in vitro for over a year the 2.3S and 2.3Q cell lines were capable of generating tumours when injected subcutaneously into mice. The transformation of these cell lines was not associated with any discernible alteration in morphology or surface phenotype. Furthermore, RNA gel blot analysis has shown no significant changes in the expression of either the endogenous or the proviral c-myc genes (data not shown). It is presumed that transformation resulted from accumulation of additional genetic change(s) during long term culture.

Phenotype of Neuroepithelial Cell Lines

The majority of the cell lines generated from the neuroepithelium appear to represent cells at a very early stage of neural differentiation. They have the morphological appearance of normal neuroepithelium cultured in vitro and express similar antigenic markers (Table 1). All the cell lines express the cytokeratin intermediate filament; this marker is also found in E10 neuroepithelium but is lost during neural differentiation and is not present in mature glial or neuronal cells. A further indication that these lines are of an immature phenotype is that the majority of the cell lines (95%) do not express neurofilaments or the neuronal surface marker A2B5 (21) (also expressed on some glial cell precursors (29)) or the astrocyte-associated intermediate filament GFAP. In addition, the lines do not express the surface marker NEP6 normally present on the glial precursor cell prior to expression of GFAP. In an attempt to induce these lines to differentiate or to shift antigenic phenotype, several agents known to induce cellular differentiation, such as phorbol esters, retinoic acid, and 8-azacytidine have been used, but no surface phenotypic changes have been observed in any of the lines examined. However, IFN-$\gamma$ and acidic and basic FGF have been effective in initiating phenotype changes.

Induction of surface antigens by IFN-$\gamma$

The neuroepithelial cell lines are similar to E10 neuroepithelium in that they normally do not express surface class I and class II histocompatibility antigens. This property is also shared by mature neurons and glia; however, it has been shown that some mature neural cells can be induced to express both classes of molecules after incubation with IFN-$\gamma$ (30). It has been found in all the 140 neuroepithelial cell lines tested that classes I and II histocompatibility molecules can be induced within 48 hr after IFN-$\gamma$ treatment (Table 1). The expression of class I antigens is similarly induced on freshly isolated E10 neuroepithelium (3). However, the expression of class II antigens is not seen on normal neuroepithelium and is only found on GFAP-positive astrocytes. The significance of this finding is unclear, although it may indicate that these lines are biased toward the glial differentiation pathway. As shown in FIG. 2A the pretreatment of the neuroepithelial cell lines with IFN-$\gamma$ has no effect upon endogenous or proviral c-myc gene expression.

FGF Stimulates Differentiation

Acidic and basic FGF are found in relatively high concentrations in the brain (31) and have been shown to enhance neuronal survival in vitro and in vivo (32). Results from our laboratory-indicate that FGF is a potent proliferative stimulus to freshly isolated E10 neuroepithelium and, at concentrations>5 ng/ml, induced morpho-differentiation. Cells from the 2.3D cell line were incubated with FGF (5 ng/ml) and showed obvious morpholical changes within 24 hr of incubation, and some of the cells begin to round up and form aggregates that sometimes detached from the plate. Staining of coverslips of these lines after treatment with FGF for the presence of neuronal and glial markers has revealed cells containing GFAP as well as a process bearing population that is both A2B5-positive and also contains neurofilament protein. A large percentage of the cells (40–50%) express neurofilaments by 3 days, whereas GFAP is not detected until 7 days after the addition of FGF.

TABLE 1

Phenotype of neuroepithelial cell lines

| Cell(s) | Antibody markers | | | |
| --- | --- | --- | --- | --- |
| | A2B5 | GFAP | NEP6 | IAI* |
| E10NE | − | − | − | − |
| 2.3D, 2.3S, and 2.3Q. | − | − | − | + |
| 95% of lines screened | − | − | − | + |
| 2.3A | + | − | − | + |
| 2.3R | − | + | − | + |

Cells cultured on glass coverslips were examined for expression of various markers by immunofluorescence with the following antibodies:
A2B5, anti-ganglioside; anti-GFAP; K2F2, anti-cytokeratin; WEHY-NEP-6, anti-glial cell precursor; anti-H-2K$^k$ monoclonal antibody clone 11-4.1; and anti-I-A$^k$ monoclonal antibody clone 10-2-16.
All cells listed were K2F2-positive, H-2-negative, H-2-positive in the presence of IFN-$\gamma$, and I-A-negative. The antigenic phenotype of the E10 neuroepithelium (NE) was similar to that of 95% of the cell lines screened.
−, Absence of marker;
+, presence of marker.
*Cells were incubated with IFN-$\gamma$ (1 unit/ml) for 24 hr prior to staining; +, indicates the ability to express these antigens in the presence of IFN-$\gamma$.

EXAMPLE 2

(a) EXPERIMENTAL PROCEDURES

Construction of Zen-myc Retroviruses

Figure 3:
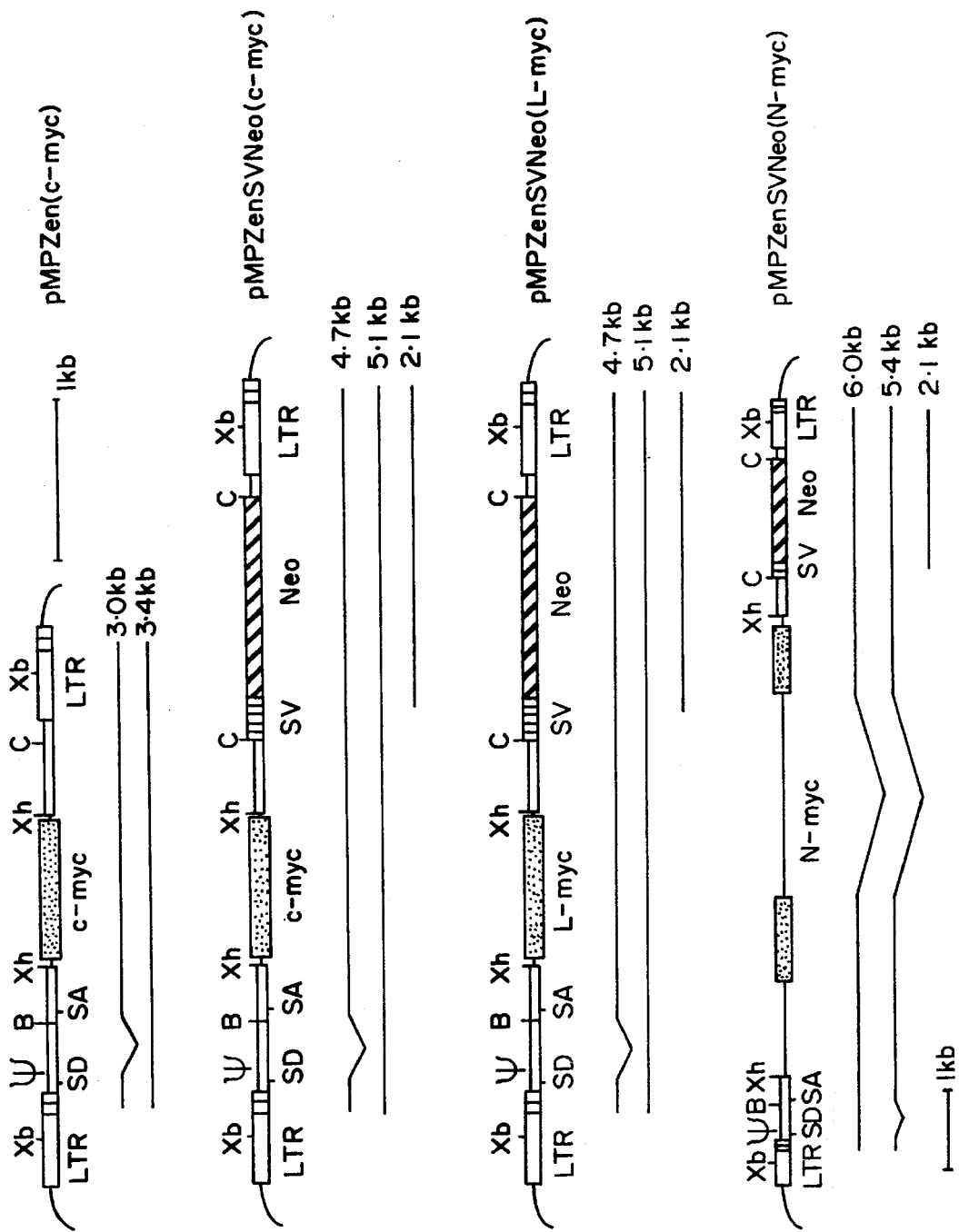
FIG. 3 is a schematic representation of retroviruses expressing c-myc, N-myc and L-myc. All the vectors have a pBR322 backbone for replication in E.coli. SD and SA indicate splice donor and slice acceptor respectively. $\psi_2$ denotes the packaging signal. SV indicates SV40 origin of replication. The three transcripts expected from the provirus are shown. Restriction endonuclease sites are abbreviated as follows: Xh, XhoI; Xb, XbaI; C, ClaI; B, BamHI.

The retroviral vectors used in these experiments, pZen, pMPZen, pZenSVNeo and pMPZenSVNeo (11) were derived from pZipNeoSV(33) and from a variant plasmid pMPZipNeo containing the enhancer from the LTR of the myeloproliferative sarcoma virus (34). The pZen(myc), pMPZen(c-myc) pZenSVNeo(c-myc) and pMPZenSV-Neo(c-myc) were constructed by insertion of the 1391 bp XhoI fragment of the murine c-myc cDNA (19) into the XhoI site of the pZen, pMPZen, pZenSVNeo and pMPZenS-VNeo vectors. The pMPZenSVNeo(N-myc) vector was constructed by insertion of the 4160 bp HindIII/SacII fragment of the murine N-myc gene (35) into the XhoI site of the pMPZenSVNeo vector DNA. This fragment contains exons 2 and 3, 820 bp of IVS-1, IVS-2 and 70 bp of the 8' untranslated region. The pMPZenSVNeo(L-myc) vector was constructed by insertion of 1400 bp SacI/HindIII fragment containing the murine cDNA clone. The L-myc cDNA was constructed by ligating the SacI/StuI fragment isolated from exon 2 of the genomic L-myc clone (9) and the StuI/HindIII fragment of the L-myc cDNA clone (9). This full length cDNA construct contains 166 bp of the 5' untranslated region, the complete L-myc coding sequences and 42 bp of the 3' untranslated region (FIG. 3).

Generation of $\psi_2$ virus producing lines $\psi_2$ cells (20) were transfected with retroviral plasmid DNA using electroporation apparatus (Biorad). 5 or 10 μg of plasmid DNA were mixed with 1×10$^6$$\psi_2$ cells in 0.8 ml of DMEM supplemented with 10% calf serum (when the retrovital plasmid DNA did not contain the SVNeo gene 30μg of retroviral plasmid were mixed with 3μg of pSV2Neo plasmid DNA (18)). The cells were incubated at 4° for 10 min prior to electropotation. They were then pulsed with 500 volts and25 μF and allowed to stand on ice for a further 5 min prior to plating onto 8 dishes (10 cm) in DMEM supplemented with 10% calf serum. After 48 hrs fresh medium containing 400 μg/ml of G418 was added and resistant colonies became evident 10–14 days after transfection, they were ring cloned and expanded for further analysis.

Infection of Neuroepithelial Cells

Infection of neuroepithelial cells was performed in exactly the same way as in Example 1.

Immunofluorescent Staining

Immunofluorescent staining was performed by the method described in Example 1.

Growth Factors

Acidic FGF from bovine brain was obtained from R & D systems, Minneapolis Minn, USA; recombinant human EGF, recombinant bovine bFGF, recombinant human IGF-I(Thr-59) and recombinant PDGF(v-sis) were obtained from Amersham, Buck.,UK. IGF-II (CR-multiplicator stimulating activity) and NGF (2.5S) were from Collaborative Research, Mass., USA. Growth factors were added to the cell lines at the following concentrations: EGF, 50 ng/ml; IGFI, 50 ng/ml; PDGF, 50 ng/ml; NGF, 50 ng/ml; bFGF, 5 ng/ml; aFGF, 5 ng/ml; IGFII, 100 ng/ml.

Cell Proliferation Assay

Cells were harvested from high density cultures of each cell line, washed 3× with DMEM containing 1% FCS and 10 μl of cells at $1\times10_4$/ml were plated onto 60 well HLA plates (Terasaki plates). Growth factors or conditioned medium from the different cell lines were then added to the cultures and the plates were incubated for 48–72 hrs. After incubation the number of cells was determined by counting under an inverted phase microscope at 100× magnification. To exclude non-viable cells Eosin was added to each well (2 min) prior to counting.

Analysis of RNA and DNA

DNA was prepared from $5\times10_6$ cells by lysis with guanidine hydrochloride (36) and analysed by Southern blot hybridisation (25). PolyA-RNA was prepared as described by Gonda et.al.(27). Samples of 2 μg were fractionated on 1% formaldehyde/agarose gel as previously described (38). The c-myc probe was the XhoI fragment of the c-myc cDNA clone pMc-myc54 (19) while the N-myc probe was the HindII/SacII fragment containing exons 2 and 3 of the N-myc genomic clone (35). The probes were labelled with $\alpha(^{32}P)$ dATP using a random hexamer priming kit (Besatec Limited, South Australia).

Western Blots

Cell lysates were prepared from approximately $2\times10^7$ cells at log phase. Cells were scraped from dishes with a rubber policeman, washed twice with PBS pH 7.5 and lysed immediately in 1ml of sample buffer (0.1 MTris pH 6.8, 10% glycerol, 0.1% triton X-100). The lysates were sonicated, centrifuged, and the supernatants aliquoted and stored at−70°C. until used. All lysates were used within 2 weeks of preparation. 80 μg of cell lysate proteins were fractionated on 10% SDS-polyacrylamide gel and electroblotted onto nitrocellulose paper (39). Following transfer the filter was washed in PBS and pre-incubated for 30 min in PBS containing 5% nonfat dried milk. The filter was then incubated for 2 hrs with sheep anti-myc oncoprotein antibody (DCP801 Cambridge Research Biochemicals) diluted 1:100, washed and further incubated for 1 hr with rabbit anti-sheep IgG. After washing, the filter was incubated for 1 hr with $^{125}I$-protein A ($1\times10^5$ cpm/ml, 40 μci/μg), washed and autoradiographed at−70°C. All incubations were at room temperature. After exposure, the nitrocellulose containing the myc protein was cut out and counted in λ counter to estimate the amount of myc protein in the different cell lines.

(b) Results

Generation of neural cell lines with new N-myc, c-myc and L-myc retroviruses

It has been shown previously that the Dol(c-myc) retrovirus can immortalise neural precursors and that the lines so generated retain characteristics of early neural cells and do not spontaneously differentiate (see Example 1). The effects of higher levels of constitutive N-myc, c-myc and L-myc expression on neuroepithelial cells has been investigated utilising a family of new. retroviral vectors, the Zen vectors (11) (FIG. 3) which were shown to express high levels of the inserted genes. These vectors were derived from the previously described ZipNeoSV(X) (33) and pMPZipNeo (34). The Zen vectors all expressed the inserted gene from a spliced subgenomic mRNA and utilise either the Moloney virus enhancer sequence (pZen,pZenSVNeo) or that from the myeloproliferative sarcoma virus (pMPZen,pMPZenSVNeo). The N-myc, c-myc and L-myc retroviral vectors were constructed by insertion of the genomic N-myc HindII/sacII fragment, the XhoI fragment of the c-myc cDNA, and a L-myc cDNA construct, respectively, into the XhoI site of the pZen vectors (see experimental procedures).

N-myc, c-myc and L-myc virus producing lines were generated by electroporating the retroviral plasmid DNA into $\psi_2$ cells together with the plasmid pSVNeo where necessary. Colonies were selected in G418 expanded and assayed directly for their capacity to immortalise E10 neuroepithelial cells as previously described (Example 1). In brief, $5\times10^5$ virus producing $\psi_2$ cells, plated onto 24-well Linbro plates, were irradiated with 2800 rads prior to addition of single cell suspensions of E10 neuroepithelial cells at various concentrations ranging from $10^3$ to $5\times10^5$ cells per well. Of the two $\psi_2$ lines producing MPZenSV-Neo(N-myc) virus, one had the capacity to immortalise E10 neuroepithelial cells. This cell line, $\psi_2$NZen6 was used to generate all the neuroepithelial lines immortalised with N-myc. All the six $\psi_2$ lines producing MPZenSVNeo(c-myc) viruses and the two $\psi_2$ lines producing MPZen(c-myc) and Zen(c-myc) viruses were capable of immortalising E10 neuroepithelium. However, only two of the six $\psi_2$ producing ZenSVNeo(c-myc) viruses were capable of immortalising E10 neuroepithelial cells. The titers of the N-myc and c-myc viruses produced by the $\psi_2$ lines capable of immortalising neuroepithelial cells were found to be between $1\times10^5$–$5\times10^5$ colony forming units per ml (17).

Cells Infected With c-myc or N-myc Zen Viruses Can Differentiate Spontaneously in vitro into Neuronal and Glial Cells Mock-infected neuroepithelial cells formed small aggregates which disappeared within one week. In marked contrast, within one week of infection, neuroepithelial cells infected with the myc viruses formed large aggregates of cells that express the neural marker A2B5 which is characteristic of the neuronal cells but is also expressed by some glial precursors (2a). In addition, a large number of these cells also expressed neurofilaments. The cells did not however, express the glial cell marker glial fibrillary acidic protein (GFAP). The size of the aggregates increased with time and networks of neuronal like cells were observed both in the aggregates and in the surrounding flat cells attached to the dish. All 48 culture wells contained cells of identical morphology. After two weeks, some cells in each well expressed the glial cell marker, GFAP. However, these cells were distinct from those expressing the A2B5 and neurofilaments, The morphology as well as the heterogeneity of these cell lines was maintained during the first 5–6 passages.

Each cell line was examined by fluorescence immunocytochemistry for the presence of the neural marker A2B5, for the neurofilament marker identifying neurons and for GFAP, the marker of glial cells (Table 2). All the lines contain cells that express both neuronal and glial cell markers, although the relative frequency of each cell type varied from line to line. Several of the cell lines have been cloned by limiting dilution, a procedure which proved difficult without plating the cells onto an irradiated feeder layer of 3T3 cells. The cloned lines differed from the founder cell lines, in that they mainly grew as an epithelial sheet resembling both normal E10 neuroepithelium and the previously described 2.3D cell line derived by infection of neuroepithelial cells with the Dol(c-myc) retrovirus (Example 1). However, unlike the 2.3D cell line and the other cell lines derived by infection with the Dol(c-myc) virus, the newly-generated cell lines differentiated spontaneously into both neurons and glial cells, when the cells reached high density. They also formed aggregates on the top of the epithelial-like monolayer similar to the aggregates formed during the first few days after the retroviral infection. Some of the cloned cell lines have now been passaged in vitro for overe a year and still retain the ability to spontaneously differentiate at high density, although their ability to do this appears to decrease with increasing passages. The ability of the cloned cell lines to differentiate into both neurons and glial cells indicates that immortalised bipotential neuroepithelial stem cells have been immortalised.

Clonality of the Cell Lines

Figure 4:
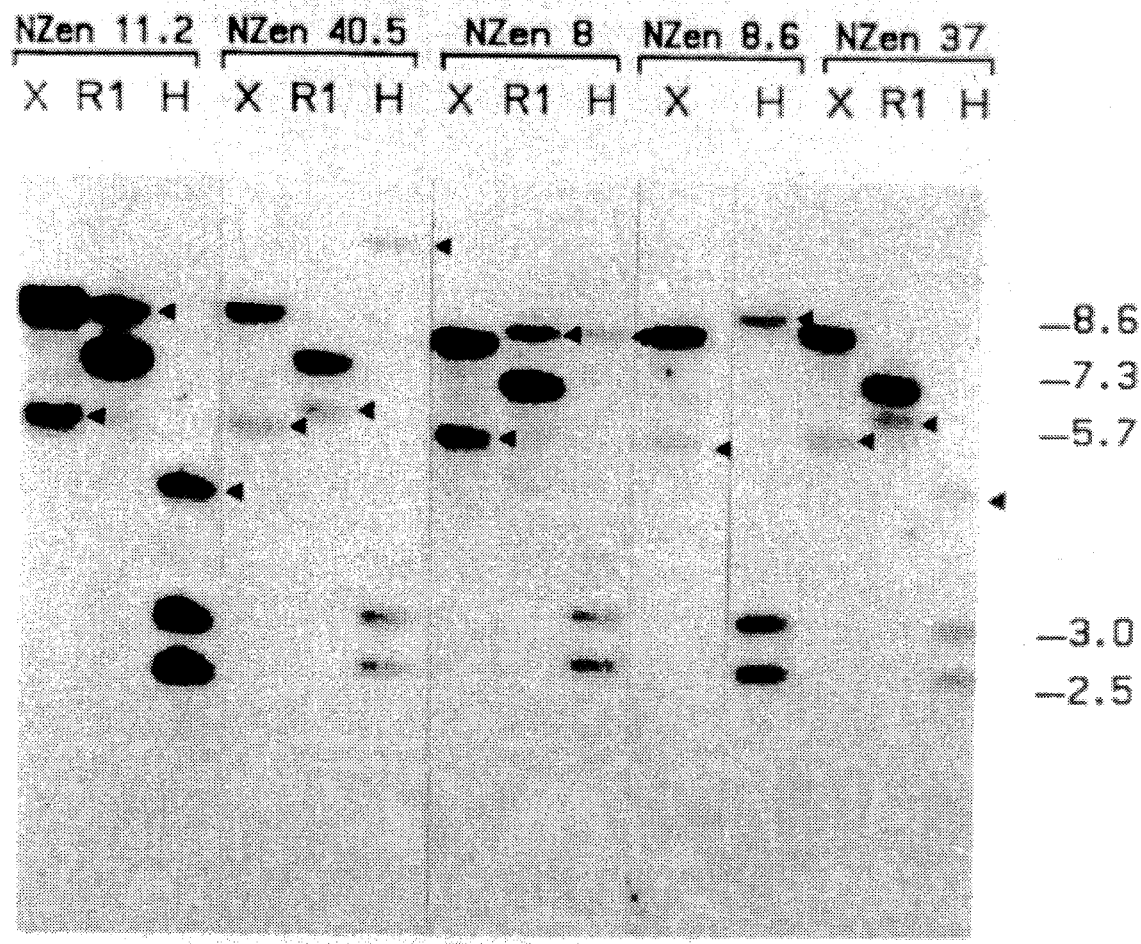
FIG. 4 shows Southern blot analysis of DNA isolated from immortalised neuroepithelial cell lines infected with MPZenSVNeo(N-myc) virus. Digests were with XbaI(X), EcoRI(RI) and HindIII(H). The probe was the SacII/HindII fragment of the mouse genomic N-myc clone (36). Arrowheads indicate the proviral N-myc fragment. Note that not all the digested DNA samples were run on the same gel.

Southern blot analysis revealed that all the cell lines harboured a full length provirus (FIG. 4). The N-myc virus-infected cell lines (designated NZen) all generated a 5.5 Kb N-myc fragment on digestion of the DNA with XbaI, which cuts once within each LTR. Thus, as expected, the N-myc intron present within the transfected plasmid was removed from the viral RNA by splicing. The DNA from most of the lines yielded a unique c-myc or N-myc bearing fragment after cutting with EcoRI or HindIII which cut only once within the retrovital vector, indicating that they derived from an integration of a single provirus copy. The presence of unique N-myc or c-myc EcoRI and HindIII fragments at intensities equivalent to half of the endogenous myc alleles indicate that the cell lines are indeed clonal.

Figure 5:
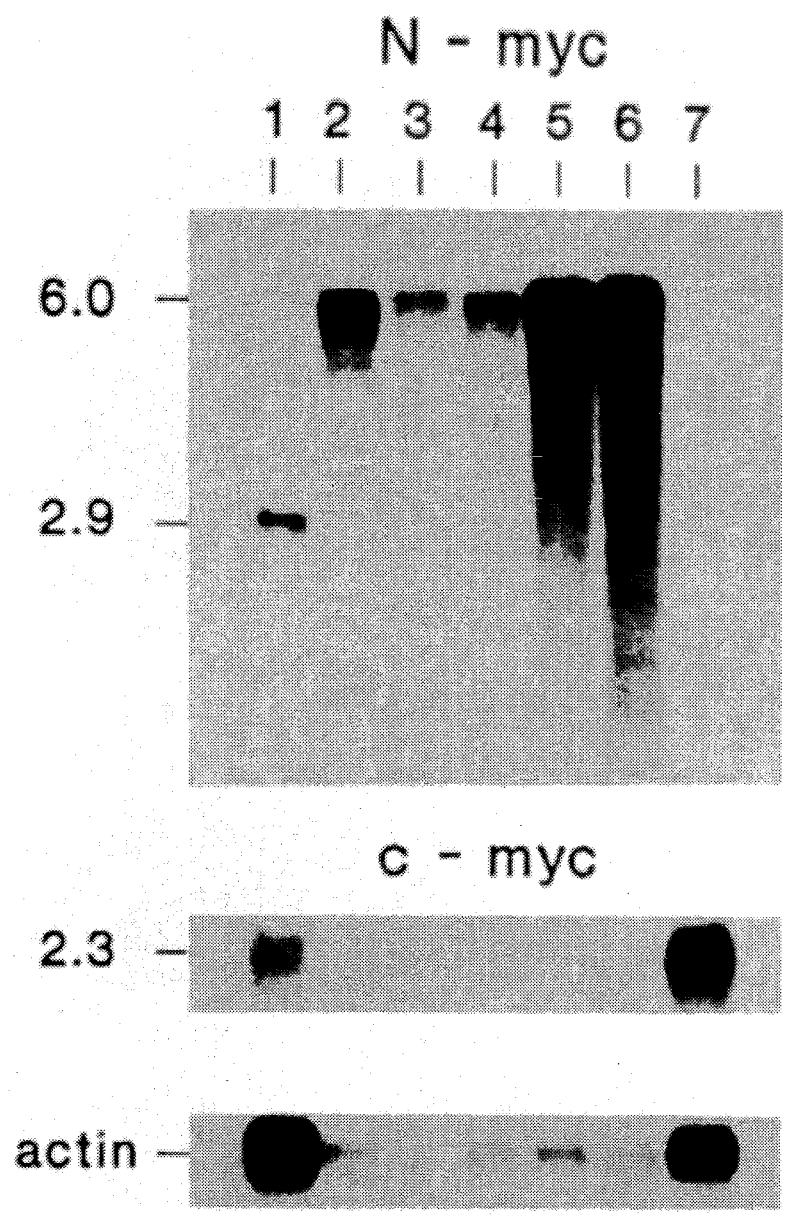

The Expression of the Cellular c-myc mRNA is Suppressed in the Neuroepithelial Cell Lines All the neuroepithelial cell lines generated by either the N-myc or the c-myc viruses expressed high levels of proviral transcripts as well as smaller processed transcripts from which the viral myc protein is translated. The N-myc virus-infected lines express a 6 Kb viral N-myc mRNA and a smaller 5.6 Kb sub-genomic N-myc mRNA. No expression of the endogenous 2.9 Kb N-myc mRNA was observed in these lines (FIG. 5, lanes 2–6). Whilst it cannot be concluded that the lack of the endogenous N-myc expression is due to suppression of the cellular allele, it is clear that in these lines cell lines c-myc expression is turned off. Like all dividing cells, E10 neuroepithelial cells express high levels of c-myc (FIGS. 5,6), however cellular c-myc expression was not detected in the N-myc infected lines even on extended exposure of the autoradiograph (FIG. 5, lanes 2–6).

Cells infected with the ZenSVNeo(c-myc) viruses and the MPZenSVNeo(c-myc) viruses also express two viral c-myc transcripts of 5.1 and 4.7 Kb (FIG. 7). While their level of expression is very high when compared to that expressed by E10 neuroepithelial cells, it is similar to that expressed by the neuroepithelial cell lines generated by infection with the Dol(c-myc) virus (FIG. 7). However, in contrast to the 2.3D cell line which also expressed the cellular c-myc, only trace amounts of cellular c-myc are expressed by the cell lines immortalised with the Zen(c-myc) virus. The cell lines infected with Zen(c-myc) (R15.1 and R15.6) and with MPZen(c-myc) (M40.4 and M40.5) viruses also express two c-myc viral transcripts of 3.4 and 3.0 Kb with similar intensities. As in the case of the ZenSVNeo(c-myc) virus-infected lines the expression of the cellular c-myc is completely suppressed.

Expression of the myc Protein in Neuroepithelia Cell Lines

The Dol(c-myc) and the Zen-myc virus-infected neuroepithelial cell lines express similar levels of myc mRNA (FIG. 7). Since the levels of mRNA expressed may not always reflect the amount of the translated protein, the levels of myc protein synthesised by the different cell lines have been measured using Western blot analysis (FIG. 8). The results in FIG. 8 indicate that the $\psi_2$ cells producing the Dol(c-myc) virus as well as the neuroepithelium cell line 2.3D generated by infection with this virus synthesise very small amounts of the c-myc proteins while the $\psi_2$ cells producing the Zen-myc viruses as well as the infected neuroepithelium cell lines produce high levels of myc protein. It was estimated by counting the different myc protein bands that the cells transfected or infected with the Zen-based viruses synthesise about 10 times more myc protein (N-myc or c-myc) than the Dol-myc cells.

Effect of Fibroblast Growth Factor on the Differentiation ofthe myc Virus Infected Cell Lines It has previously been reported that E10 neuroepithelial cells as well as the neuroepithelial cell line 2.3D can be induced to differentiate into neurons and glial cells by the addition of acidic or basic FGF (Example 1). In order to examine the effect of FGF and other growth factors on the cell lines generated with the Zen-based viruses some of the cell lines were tested with a panel of recombinant or purified growth factors known for their ability to induce cellular differentiation or to support cellular growth. All the factors used have been identified in normal brain tissue, namely, acidic and basic FGF, epidermal growth factor (EGF), nerve growth factor (NGF), platelet derived growth factor (PDGF) and insulin-like growth factor I and II (IGFI, IGFII). Interestingly, it was found that acidic and basic FGF were the only known growth factor capable of significantly influencing cellular differentiation. The effect of FGF was rapid: cell aggregation and neurofilament expression occurring within 2 days of FGF addition. When both heparin and FGF were added the response was enhanced so that 5–6 days after FGF addition, the majority of the cells formed aggregates and detatched from the glass coverslip.

TABLE 2

Phenotype of Cell Lines Obtained from E10 Neuroepithelium
Infected with Retroviruses Containing N-myc or c-yc

| Cell line | Retrovirus construct | Clonal[1] | Response to FGF[2] | Antigenic Markers Expressed[3] | | |
|---|---|---|---|---|---|---|
| | | | | GFAP | A2B5 | Neuro-filaments |
| NZen5 | MPZenSVNeo[N-myc] | + | + | + | ++ | ++ |
| NZen6 | " | – | – | – | ++ | + |
| NZen7 | " | + | + | + | ++ | ++ |
| NZen8 | " | + | + | ++ | + | ++ |
| NZen8.2 | " | + | + | –+ | ++ | ++ |
| NZen8.6 | " | + | + | –+ | ++ | ++ |
| NZen9 | " | + | + | + | ++ | ++ |
| NZen13 | " | + | – | –+ | + | + |
| NZen14 | " | N.D. | + | –+ | + | + |
| NZen15 | " | + | + | –+ | ++ | + |
| NZen17 | " | + | – | –+ | + | + |
| NZen25 | " | – | + | + | +++ | + |
| NZen36 | " | – | + | + | + | ± |
| NZen37 | " | + | – | –+ | – | + |
| R1.2 | ZenSVNeo[c-myc] | + | + | + | ++ | ++ |
| R1.3 | " | – | + | –+ | + | ++ |
| R1.4 | " | + | + | –+ | + | ++ |
| R2.2 | " | + | + | – | + | ± |
| R15.3 | MPZen[c-myc] | N.D. | + | –+ | ++ | ++ |
| R15.6 | " | + | – | –+ | ++ | +++ |
| MM4.2 | MPZenSVNeo[c-myc] | N.D. | + | – | + | ++ |
| MM4.4 | " | N.D. | + | – | ++ | +++ |
| MM5.3 | " | N.D. | – | – | + | + |
| MM5.6 | " | + | – | – | + | ++ |

[1] Cell lines were cloned by limiting dilutions and their clonality was determined by Southern blot analysis as previously described N.D. - not done.
[2] 100 cells of each of the cell lines were plated in a Terasaki well with or without 5 ng/ml bFGF in 10 μl DMEM containing 1% FCS. The assays were read 48 hrs later. The response to FGF was scored positive when the number of cells in the presence of FGF were at least twice that of the control. Each cell line was assayed in six replicate cultures.
[3] Cells were grown on coverslips at high cell density for 2 days before staining for the expression of the surface marker A2B5 and the two intermediate filament markers GFAP and neurofilaments [see experimental procedures for details]. They were examined for the expression of these markers using fluorescence microscopy. The stained cells were scored as follows: –, <2%; +1, >2%; +2, >5%; +3>, 10%.

Those skilled in the art will appreciate the significance and potential use of the production of immortalised neural precursor cells in accordance with the present invention. In particular, this invention will enable the study of neural cell lineage during brain development and provide a source of new neurotrophic factors that regulate proliferation and differentiation of neurons and glial cells for the purification and cloning of these factors. The cell lines will also provide a clonal population of target cells to assay new neurotrophic and differentiation factors, as well as providing a model system for the study of replacement of damaged nervous tissue. It will also be appreciated that the production of neurotrophic factors from these cell lines opens the way to the therapeutic application of these factors to damaged nervous tissue, in addition to the direct use of in vitro generated cells in transplantation into damaged nervous tissue.

REFERENCES:

1. Abney, E. R., Bartlett, P. F and Raff, M. C. (1981) *Dev. Biol.* 83, 301–310.
2. Bartlett, P. F., Bailey, K. A. and Wycherley, K. A. , (1987) *Neurosci. Lett. Supp.* 27, 42–43.
3. Bailey, K. A., Wycherley, K. A. and Bartlett, P. F. (1987) *Neuroses Lett. Supp.* 27, 53.
4. Alt, P. A., DePinho, R. A., Zimmerman, K., Legoug, E., Hatton, K., Ferrier, P., Tesfaye, A., Yancopoulos, G. D., Nisen, P. (1986). The human myc gene family. Cold Spring Harbor Symp. Quant.Biol. 51: 931–941.
5. Ingravsson, S., Asker, C., Axelson, H., Klein, G. and Sumagi, J. (1988). *Mol.Cell.Biol.* 8:3168–3174.
6. Land, H., Parada, L.F. and Winberg, R. A. (1983). *Nature* 304, 596–602.
7. Yancopolous, G. D., Nisen, P. D., Tesfaye, A., Kohl, N.E., Goldfarb, M. P. and Alt, F. W. (1985). *Proc.Natl.Acad.Sci.* 82:1195–1198.
8. DePinho, R., Hatton, K. S., Tesfaye, A., Yancopoulos, G. D. and Alt, F. W. (1987). *Genes and Development* 1:1311–1326.
9. Legouy, E., DePinho, R. A., Zimmerman, K., Collum, R., Yancopoulos, G. D., Kitsock, L., Kriz, R. and Alt, F. W. (1987) *EBMO J* 6: 3359–3366.
10. Zimmerman, K., Yancopoulos, G., Collum, R., Smith, R., Kohl, N., Denis, K., Nau, M., Witte, O., Toran-Allerand, D., Gee, C., Minna, J. and Alt, F. (1986). *Nature* 319: 780–783.
11. Hariharan, I. K., Adams, J. M. and Cory, S. (1988). *Oncogene Res.* (In press).
12. Mougneau, E., Lemieux, L., Rassoulzadegan, M. and Cuzin, F. (1983). *Proc.Natl.Acad.Sci. USA.* 81, 5758–5762.
13. Zerlin, M., Julius, M. A., Cerni, C. and Marcu, K. B. (1987). *Oncogen* 1, 19–27.
14. Cowan, W. M., (1979). *Sci. American.* 241(3), 106–117.
15. Weston, J. A. (1970). *Adv. Morphogen.* 8, 41–114.
16. Gospodarowicz, D. (1985). In Ford, R. J. and Maizel, A. L. (eds). "Mediators in Cell Growth and Differentiation." Raven Press, New York, NY pp109–134.

17. Cory, S., Bernard, O., Bowtell, D., Schrader, S., and Schrader, J. W. (1987), *Oncogene Res.* 1: 67–76.
18. Southern, P. J. and Berg, P. (1982). *J.Mo.Appl. Genet.* 1, 327–344.
19. Stanton, L., Watt, R. and Marcu, K. B. (1983) *Nature (London)* 303: 401–406.
19a. Reed, K. C. and Mann, D. A. (1985) *Nucleic Acids Res.* 13: 7207–7221.
20. Mann, R., Mulligan, R. C. and Baltimore, D. (1983). *Cell* 33,153–159.
21. Eisenbarth, G. S., Walsh, F. S. and Nirenberg, M. (1979). *Proc.Natl.Acad.Sci. USA.* 76, 4913–4917.
22. Drager, U. C., Edward, D. L. and Kleinschmidt, J. (1983). *Proc.Natl.Acad.Sci.USA* 80:6408–6412.
23. French, P. W. and Hewish, D. R. (1986) *J.Cell.Biol.* 102: 1412–1418.
24. Oi, V. T., Jones, P. O., Goding, J. W. and Herzenberg, L. A. (1978) *Cur.Top.Microbiol. Immunol.* 81:115–129.
25. Southern, E. M. (1975), *J.Mol.Biol.* 98: 503–517.
26. Adams, J. M., Harris, A. W., Pinkert, C. A., Corcoran, L. M., Alexander, W. S., Cory, S., Palmiter, R. D. and Brinster, R. L. (1985). *Nature (London)* 318: 533–538.
27. Alexander, W. S., Schrader, J. W. and Adams, J. M. (1982) *Mol.Cell.Biol.* 7: 1436–1444.
28. Keath, E. J., Caimi, P. G. and Cole, M. D. (1985) *Cell* 39: 339–348.
29. Raff, M. C., Miller, R. H. and Noble, M. (1983) *Nature (London)* 303: 390–396.
30. Wong, G. H. W., Bartlett, P. F., Clark-Lewis, I., McKimm-Breschkin, J. L. and Schrader, J. W. (1984) *Nature (London)* 310:688–691.
31. Gospodarowicz, D., Cheng, J., Lui, G. M., Baird, A. and Bohlent, P. (1984). *Proc. Natl.Acad.Sci.USA* 81:6963–6967.
32. Morrison, R. S., Sharma, A., deVellis, J. and Bradshaw, R. A. (1986). *Proc.Natl.Acad.Sci.USA* 83:7537–7541.
33. Cepko, C. L., Roberts, B. E. and Mulligan, R. C. (1984). *Cell* 37:1053–1062.
34. Bowtell, D. D. L., Johnson, G. R., Kelso, A. and Cory, S. (1987). *Mol.Biol.Med.* 4:229–250.
35. DePinho, R., Legouy, E., Feldman, L. R., Kohl, N., Yancopoulos, G. D. and Alt, F. W. (1986). *Proc.Natl.Acad.Sci.USA* 83: 1827–1831.
36. Bowtwell, D. D. L. (1987). *Anal.Biochem.* 162: 463–465.
37. Gonda, T. J., Sheivess, D. and Bishop, J. M. (1982). *Mol.Cell.Biol.* 2: 617–624.
38. Thomas, P. S. (1980). *Proc.Natl.Acad.Sci.USA* 77: 5201–5203.
39. Towbin, H., Staehelin, (T) and Gordon, J. (1979). *Proc.Natl.Acad.Sci.USA* 4350.

We claim:

1. An cell line comprising mammalian neuroepithelial or neural crest cells which have been infected with a retroviral vector carrying a c-myc or N-myc oncogene and in which said c-myc or N-myc gene is expressed.

2. A method for the in vitro production of immortalized mammalian neural precursor cells which comprises infecting mammalian neuroepithelium or neural crest cells with a retroviral vector carrying a c-myc or N-myc oncogene to provide infected cells, wherein said neuroepithelium or neural crest cells are capable of being infected by said retroviral vector, and under conditions whereby the c-myc or N-myc gene is expressed in said infected cells.

3. A method according to claim 2 wherein said retroviral vector comprises the vector pDol carrying the c-myc oncogene.

4. The method according to claim 3 wherein infection of mammalian neuroepithelium or neural crest cells with said retroviral vector is accomplished by:

(a) transfecting fibroblast cells with said retroviral vector to produce virus-producing fibroblast cells, wherein said fibroblast cells are capable of being transfected by said retroviral vector, expressing retrovirus genes borne by said vector, and producing and packaging retroviral particles; and (b) co-cultivating said virus-producing fibroblast cells with said neuroepithelial or neural crest cells to infect said neuroepithelial or neural crest cells with said retroviral vector.

5. A method according to claim 2, wherein said immortalised neural precursor cells are induced with acidic or basic fibroblast growth factor to differentiate to form at least one of neuronal cells and glial cells.

6. The method according to claim 2 wherein said immortalised neural precursor cells do not differentiate spontaneously in vitro.

7. The method according to claim 2 wherein said retroviral vector comprises a vector selected from the group consisting of pZen, pZenSVNeo, pMPZen and pMPZenSVNeo.

8. The method according to claim 7 wherein infection of mammalian neuroepithelium or neural crest cells with said retroviral vector is accomplished by: (a) transfecting fibroblast cells with said retroviral vector to produce virus-producing fibroblast cells, wherein said fibroblast cells are capable of being transfected by said retroviral vector, expressing retrovirus genes borne by said vector, and producing and packaging retroviral particles; and (b) co-cultivating said virus-producing fibroblast cells with said neuroepithelial or neural crest cells to infect said neuroepithelial or neural crest cells with said retroviral vector.

9. The method according to claim 8, wherein said imortalised neural cells are induced with acidic or basic fibroblast growth factor to differentiate to form at least one of neuronal cells and glial cells.

10. The cell line according to claim 1, wherein said retrovital vector comprises the vector pDol carrying the c-myc oncogene.

11. A cell line according to claim 1, wherein said retroviral vector comprises a vector selected from the group consisting of pZen, pZenSVNeo, pMPZen and pMPZenSVNeo, carrying either the c-myc or the N-myc oncogene.

12. The method of claim 4 wherein the fibroblast cells are psi-2 cells.

* * * * *

UNITED STATES PATENT AND TRADEMARK OFFICE
CERTIFICATE OF CORRECTION

PATENT NO. : 5,580,777

DATED : December 3, 1996

INVENTOR(S) : Ora Bernard, et al.

It is certified that error appears in the above-identified patent and that said Letters Patent is hereby corrected as shown below:

On the Title Page, section [63], line 2: "536,423" should read --536,623--
Column 2, line 26: "Which should read --which--
Column 4, line 8: "FIG." should read --FIG. 5--
Column 5, line 58: "Interferono" should read --Interferon--

Column 6, line 42: "EXPRESSION oF" should read --Expression of--
Column 8, line 63: "and25μF" should read --and 25μF--
Column 9, line 40: "SaciI" should read --SacII--
Column 10, lines 65-66: "neurofilaments, The" should read --neurofilaments. The--
Column 12, line 41: "ofthe" should read --of the--
Column 13, line 3: "c-yc" should read --c-myc--

Column 15, line 44: "Bowtwell" should read --Bowtell--
Column 15, line 49: "5201∝5203" should read --5201-5203--
Column 15, line 51 "USA 4350" should read --USA 76: 4350--
Column 15, line 56, Claim 1: after "expressed" insert --, and wherein said expression immortalizes said cells--

Signed and Sealed this

Thirtieth Day of June, 1998

Attest:

BRUCE LEHMAN

Attesting Officer    Commissioner of Patents and Trademarks